(12) United States Patent
Cheng

(10) Patent No.: US 12,708,765 B1
(45) Date of Patent: Aug. 18, 2026

(54) ELECTRIC SHOCK COVER

(71) Applicant: Xiangying Cheng, Dongguan (CN)

(72) Inventor: Xiangying Cheng, Dongguan (CN)

( * ) Notice: Subject to any disclaimer, the term of this patent is extended or adjusted under 35 U.S.C. 154(b) by 0 days.

(21) Appl. No.: 19/409,738

(22) Filed: Dec. 5, 2025

(30) Foreign Application Priority Data

Aug. 6, 2025 (CN) ........................ 202521673211.1

(51) Int. Cl.
*A61N 1/20* (2006.01)

(52) U.S. Cl.
CPC .................................... *A61N 1/20* (2013.01)

(58) Field of Classification Search
CPC .... A61N 1/20; A61H 2201/165; A61H 19/00; A61H 2201/10; A61H 2201/5058; A61H 23/02; A61H 19/32; A61H 19/30
USPC ....... 607/143; 600/38, 39; 601/5, 15, 18, 23, 601/84; 602/6, 14, 67, 70, 72; 606/41
See application file for complete search history.

(56) References Cited

U.S. PATENT DOCUMENTS 11,701,247 B2 * 7/2023 Madore ..................... A61F 5/37 128/883
2008/0065187 A1 * 3/2008 Squicciarini ........... A61H 23/02 600/38
2011/0295156 A1 * 12/2011 Arturi ...................... A61N 1/22 600/587
2012/0172661 A1 * 7/2012 Chiu ....................... A61F 7/007 600/38
2014/0073851 A1 * 3/2014 Gioia ........................ A61F 5/41 600/38
2022/0105342 A1 * 4/2022 Bennett .................. A61H 19/32

* cited by examiner

*Primary Examiner* — Carl H Layno
*Assistant Examiner* — Mary Grace Schlueter
(74) *Attorney, Agent, or Firm* — Birchwood IP

(57) ABSTRACT

The present disclosure relates to an electric shock cover, including a cover body defining a protective space that matches a shape of a penis, where the protective space has an inlet. The electric shock cover further includes a first electrically conductive silicone block disposed on the cover body at a tail which is opposite the inlet and with which the penis comes into contact when the penis erects upward, and in electrical contact with the battery assembly such that the erected penis comes into contact with the first electrically conductive silicone block to effect an electric shock to the penis.

13 Claims, 3 Drawing Sheets

ELECTRIC SHOCK COVER

TECHNICAL FIELD

The present disclosure relates to the technical field of medical devices, and in particular, to an electric shock cover.

BACKGROUND

Electric shock covers in the prior art can effectively protect penises, and can better adapt to the shapes and sizes of the penises by means of a tandem fastening mechanism, and are highly adaptable, simple in structure, and easy to use. A plurality of ventilation channels are provided on a cover body. The ventilation channels communicate with a protective space to prevent heat accumulation in the protective space and facilitate ventilation so as to improve the user experience.

SUMMARY

The present disclosure aims to overcome the deficiencies of the prior art, and the following technical solution is employed.

An electric shock cover includes:

a cover body formed with a protective space that matches a shape of a penis, the protective space being formed with an inlet;

a battery assembly;

an electrically conductive silicone ring disposed at the inlet, wherein the electrically conductive silicone ring is in electrical contact with the battery assembly; and a first electrically conductive silicone block disposed on the cover body at a tail which is opposite the inlet and with which the penis comes into contact when the penis erects upward, and in electrical contact with the battery assembly such that the erected penis comes into contact with the first electrically conductive silicone block to effect an electric shock to the penis.

A further technical solution is provided. An electric shock cover includes:

a cover body formed with a protective space that matches a shape of a penis, the protective space being formed with an inlet;

a control board;

a battery assembly for powering the control board;

an electrically conductive silicone ring disposed at the inlet, wherein the electrically conductive silicone ring is in electrical contact with the control board; and a first electrically conductive silicone block disposed on the cover body at a tail which is opposite the inlet and with which the penis comes into contact when the penis erects upward, and in electrical contact with the control board such that the erected penis comes into contact with the first electrically conductive silicone block to effect an electric shock to the penis.

DETAILED DESCRIPTION OF THE PREFERRED EMBODIMENTS

The present disclosure is further described below with respect to specific embodiments and the accompanying drawings.

Figure 1:
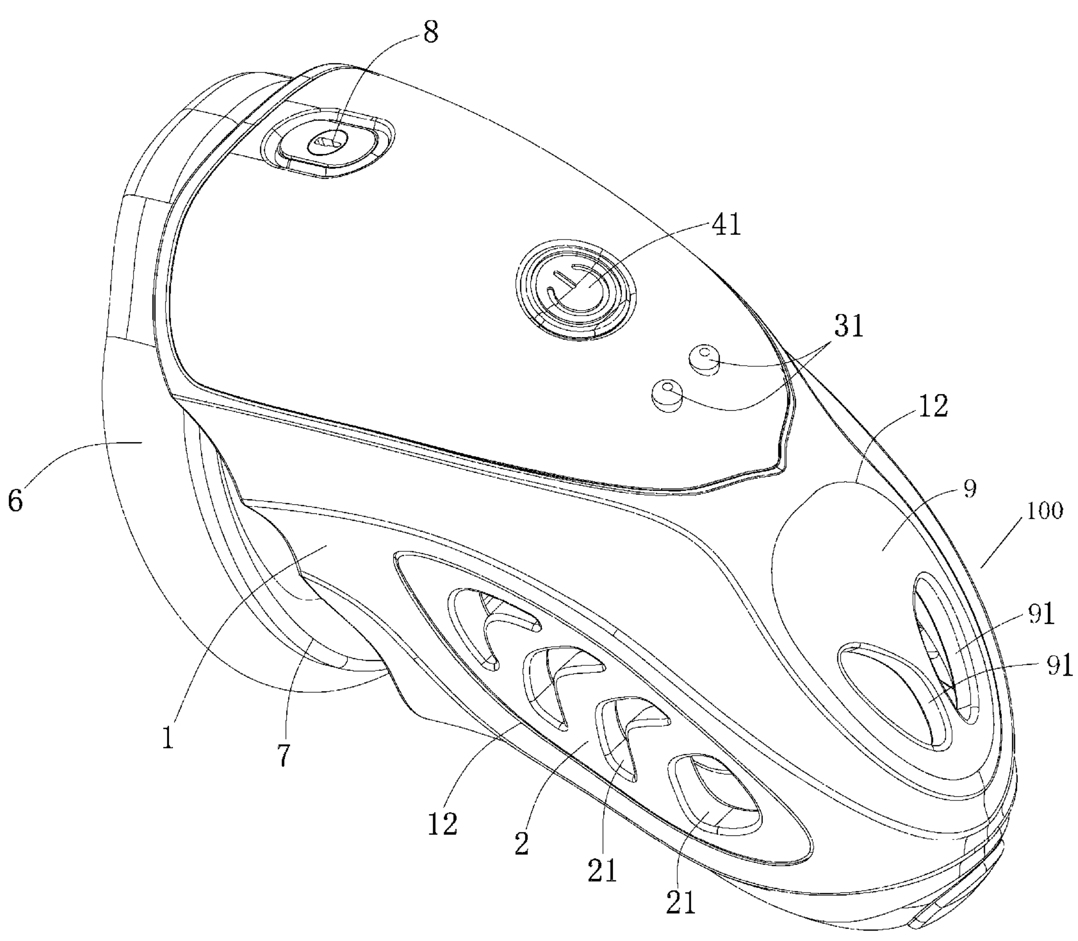
FIG. 1 is a perspective view of an embodiment of the present disclosure.
Figure 2:
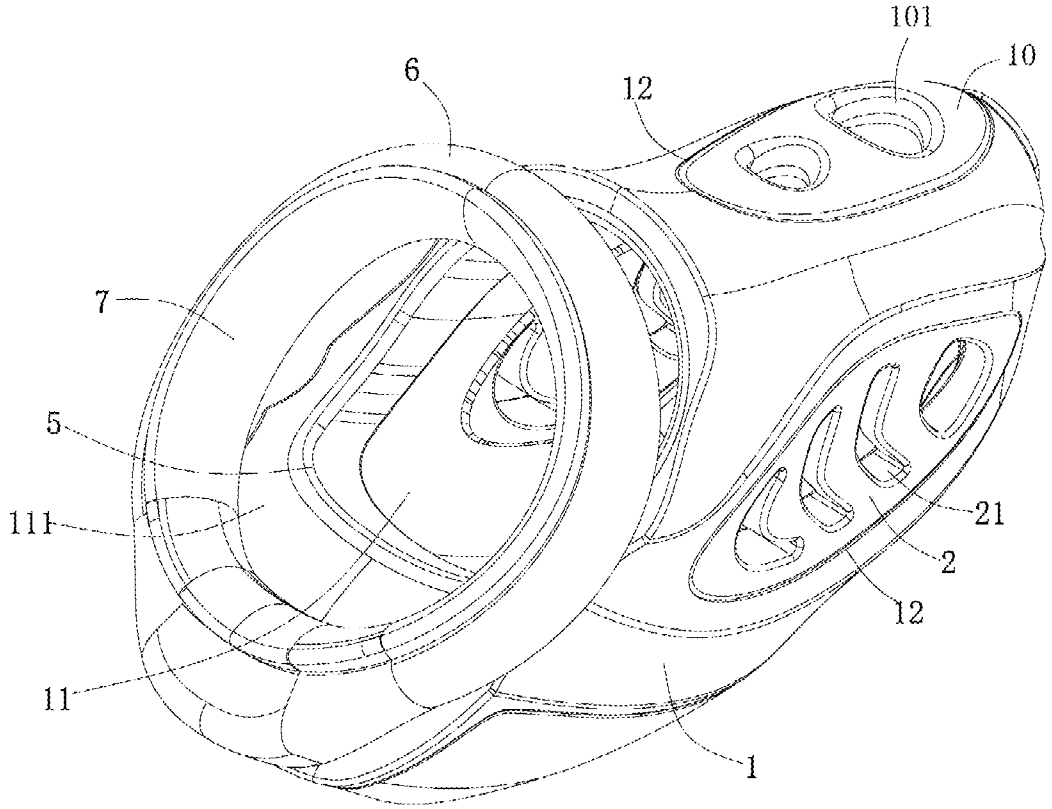
FIG. 2 is a perspective view of the embodiment of the present disclosure from another perspective.
Figure 3:
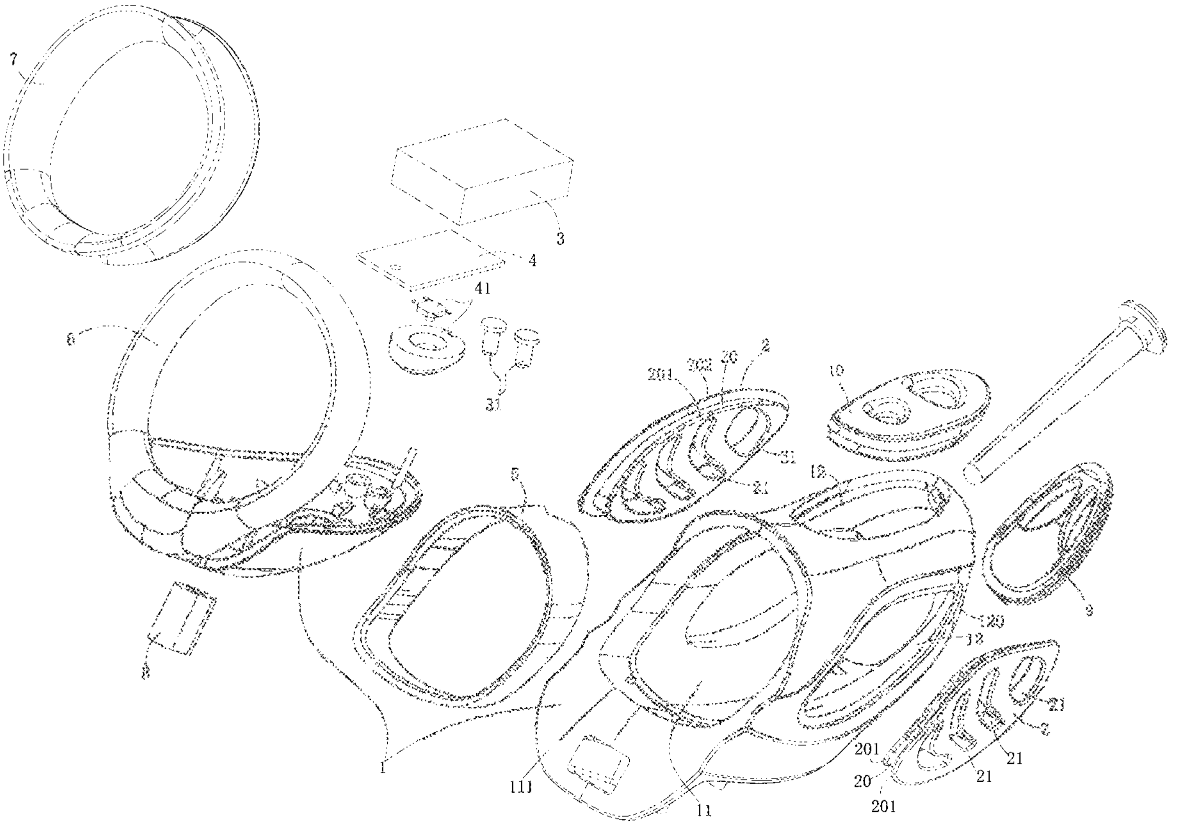
FIG. 3 is an exploded view of the embodiment of the present disclosure.

The present embodiment provides an electric shock cover. As shown in FIGS. 1-3, the electric shock cover includes a cover body 1 defining a protective space 11 that matches a shape of a penis. The protective space 11 has an inlet 111, and the cover body 1 is inwardly provided along its exterior with a plurality of ventilation channels 12 through the protective space 11. The protective space 11 of the cover body 1 envelopes the exterior of the penis, and the cover body 1 is ventilated through the ventilation channels 12 to provide more comfort to the penis. Preferably, a metal conductor is pre-embedded in the cover body 1.

The electric shock cover further includes:

a battery assembly 3;

an electrically conductive silicone ring 5 disposed at the inlet 111, where the electrically conductive silicone ring 5 is in electrical contact with one of electrodes of the battery assembly via the metal conductor; and a first electrically conductive silicone block 9 disposed on the cover body 1 at a tail 100 which is opposite the inlet 111 and with which the penis comes into contact when the penis erects upward, and in electrical contact with another electrode of the battery assembly 3 via the metal conductor, such that the erected penis comes into contact with the first electrically conductive silicone block 9 to effect an electric shock to the penis.

In order to maximize ventilation, in the embodiment of the present disclosure, two oppositely disposed removable rubber blocks 2 formed between the inlet 111 and the first electrically conductive silicone block 9 are included. Each of the removable rubber blocks 2 has at least one vent 21, and the removable rubber blocks 2 can be embedded and mounted in the ventilation channels 12 and fill the ventilation channels 12. The protective space 11 communicates with the outside through the vents 21. In the embodiment of the present disclosure, during wearing, the removable rubber blocks 2 are first embedded and mounted in the ventilation channels 12. As a result, the protective space 11 communicates with the outside through the vents 21 with a smaller size, which in turn prevents foreign objects from passing through the ventilation channels 12 and coming into contact with the penis in the protective space 11, thereby achieving the effect of better protection of the penis. When the wearing is completed and ventilation is required, the removable rubber blocks 2 can be removed from the ventilation channels 12, thereby enabling the protective space 11 to be rapidly ventilated through the ventilation channels 12. The embodiment of the present disclosure provides an excellent ventilation effect while achieving an optimal protective function.

In one embodiment, the removable rubber blocks 2 in the embodiment of the present disclosure also have a decorative effect, and a user may change the removable rubber blocks 2 of different colors or different styles depending on his preference to meet different use requirements. The removable rubber blocks 2 also serve to improve the aesthetics of the product.

In one embodiment, the first electrically conductive silicone block 9 is fixed by means of embedding, snap-fit or press-fit.

In one embodiment, the removable rubber blocks 2 are assembled with the ventilation channels 12 as follows. Each of the removable rubber blocks 2 is formed with an embedding groove 20 on a periphery, the removable rubber blocks 2 are embedded in the ventilation channels 12, and then the embedding grooves 20 envelope and are assembled with inner walls of the ventilation channels 12, providing a stable assembly structure which makes the unintentional disengagement of the removable rubber blocks 2 impossible.

Specifically, each of the removable rubber blocks 2 is formed with an inner flange 201 on an inner side of its periphery, the removable rubber block 2 is formed with an outer flange 202 on an outer side of the periphery, and the embedding groove 20 is formed between the periphery of the removable rubber block 2 and the inner flange 201 and the outer flange 202. Correspondingly, a stepped groove 120 is formed at an outer edge of each of the ventilation channels 12, and the outer flange 202 is embedded in the stepped groove 120, such that a more stable assembly structure is formed, and an outer wall of the removable rubber block 2 is smoothly joined to an outer wall of the cover body 1 to ensure a more aesthetic appearance of the embodiment of the present disclosure. In one embodiment, the first electrically conductive silicone block 9 has at least one hollowed-out portion 91, and the protective space 11 communicates with the outside through the hollowed-out portion 91.

The cover body 1 is further provided with a fastening ring 6. A soft rubber sleeve 7 is sleeved on a surface of the fastening ring 6. The soft rubber sleeve 7 has a passage for the penis to pass through which is located beside the inlet 111 of the protective space 11 and which corresponds to inlet 111. The fastening ring 6 is in contact with the penis via the soft rubber sleeve 7, which can enhance wearing comfort and prevent damage to the penis. The fastening ring 6 also has the effect of positioning the wearing. In one embodiment, the soft rubber sleeve 7 has a C-shaped cross section, is sleeved on an inner surface of the fastening ring 6 from inside to outside, and does not wrap an outer surface of the fastening ring 6.

The fastening ring 6 is removably mounted on the cover body 1 and is locked by a lock 8. Particularly, after the fastening ring 6 is sleeved on the penis, the fastening ring 6 is locked to the cover body 1 by the lock 8 to enhance the wearing stability.

In some embodiments, the battery assembly 3 and a control board 4 electrically connected to the battery assembly 3 are provided in the cover body 1. The control board 4 is electrically connected to the first electrically conductive silicone block 9 and outputs micro-currents to the first electrically conductive silicone block 9, an inner wall of the first electrically conductive silicone block 9 is exposed in the protective space 11, and the penis, when erects and becoming thicker, comes in to contact with the first electrically conductive silicone block 9 to form a closed loop with the battery assembly 3 or the control board 4 to which the electrically conductive silicone ring 5 is connected, thereby allowing the micro-currents to be transmitted to the penis to realize a micro-electric shock, which in turn induces detumescence of the penis such that the penis no longer erects and become thicker.

In some embodiments, the cover body 1 is provided with charging contacts 31 for charging the battery assembly 3, and the cover body 1 is further provided with a control switch 41 electrically connected to the control board 4.

In some embodiments, the electrically conductive silicone ring 5 is further provided at the inlet 111 of the protective space 11, the electrically conductive silicone ring 5 is in electrical contact with the first electrically conductive silicone block 9, and the electrically conductive silicone ring 5 is electrically connected to the battery assembly 3 or the control board 4. The electrically conductive silicone ring 5 is also used to transmit micro-currents. The micro-currents are output through the control board 4 to the electrically conductive silicone ring 5 when the penis erects, and are transmitted by the electrically conductive silicone ring 5 to the penis. In addition, the electrically conductive silicone ring 5 also transmits the micro-currents to the first electrically conductive silicone block 9, and the micro-currents are transmitted by the first electrically conductive silicone block 9 to the penis penetrates and is attached to the protective space 11, thereby achieving a multi-point (multi-site) micro-electric shock, which in turn induces detumescence of the penis such that the penis no longer erects and become thicker.

In some embodiments, the metal conductor is pre-embedded in the cover body 1. the metal conductor is in contact connection with the electrically conductive silicone ring 5 at one end and is in contact connection with the battery assembly 3 or the control board 4 at the other end. Alternatively, the electrically conductive silicone ring 5 is electrically connected to the battery assembly 3 or the control board 4 by a wire.

In one embodiment, the cover body 1 is further provided with a second electrically conductive silicone block 10 opposite the first electrically conductive silicone block 9, and the second electrically conductive silicone block 10 is electrically connected to the electrically conductive silicone ring 5, such that the first electrically conductive silicone block 9 is electrically connected to the second first electrically conductive silicone block 10 to generate micro-currents when the penis erects and becomes thicker. The second electrically conductive silicone block 10 is also provided with air vents 101.

In the embodiment of the present disclosure, in specific use, the first electrically conductive silicone block 9 is first embedded and mounted in the ventilation channel 12 and fills the ventilation channel 12. As a result, the protective space 11 communicates with the outside through the vents 21 with a smaller size, which in turn prevents foreign objects from passing through the ventilation channel 12 and coming into contact with the penis in the protective space 11, thereby achieving the effect of better protection of the penis. When the wearing is completed and ventilation is required, the first electrically conductive silicone block 9 can be removed from the ventilation channel 12 to reveal the ventilation channel 12 with a larger size. Thus, the protective space 11 can be rapidly ventilated through the large-sized ventilation channel 12 to provide an ideal ventilation effect. The embodiment of the present disclosure provides an excellent ventilation effect while achieving an optimal protective function.

Of course, the foregoings are merely specific embodiments of the present disclosure and are not intended to limit the scope of implementation of the present disclosure, and equivalent changes or modifications made to the constructions, features and principles without departing from the patent application scope of the present disclosure shall fall within the patent application scope of the present disclosure.

What is claimed:

1. An electric shock cover, comprising:

a cover body formed with a protective space that matches a shape of a penis, the protective space being formed with an inlet;

a battery assembly;

an electrically conductive silicone ring disposed at the inlet, wherein the electrically conductive silicone ring is in electrical contact with the battery assembly; and a first electrically conductive silicone block is removably disposed in a first ventilation channel on the cover body at a tail which is opposite the inlet and with which the penis comes into contact when the penis erects upward, and surrounds the protective space together with the cover body, and in electrical contact with the battery assembly such that the erected penis comes into contact with the first electrically conductive silicone block to effect an electric shock to the penis, wherein the first electrically conductive silicone block has at least one hollowed-out portion, and the protective space communicates with the outside air through the hollowed-out portion.

2. The electric shock cover according to claim 1, wherein the first electrically conductive silicone block is fixed by means of embedding, snap-fit or press-fit.

3. The electric shock cover according to claim 1, wherein the cover body is provided with charging contacts for charging the battery assembly.

4. The electric shock cover according to claim 1, wherein the cover body is further provided with a second electrically conductive silicone block opposite the first electrically conductive silicone block, the second electrically conductive silicone block being electrically connected to the electrically conductive silicone ring.

5. The electric shock cover according to claim 1, wherein second ventilation channels are further formed between the inlet and the first electrically conductive silicone block, and removable rubber blocks are provided in the second ventilation channels.

6. The electric shock cover according to claim 5, wherein each of the removable rubber blocks is formed with an inner flange and an outer flange on a periphery, an embedding groove being formed between the inner flange and the outer flange.

7. The electric shock cover according to claim 6, wherein a stepped groove is formed at an outer edge of each of the second ventilation channels, and the outer flange is embedded in the stepped groove such that an outer wall of the removable rubber block is smoothly joined to an outer wall of the cover body.

8. The electric shock cover according to claim 7, wherein at least one vent is provided on the removable rubber block and is configured to allow the protective space to communicate with outside air.

9. The electric shock cover according to claim 8, wherein two removable silicone blocks are comprised and are formed oppositely between the inlet and the first electrically conductive silicone block.

10. The electric shock cover according to claim 1, wherein the cover body is further provided with a fastening ring, a soft rubber sleeve being sleeved on a surface of the fastening ring.

11. The electric shock cover according to claim 10, wherein the fastening ring is removably mounted on the cover body and is locked by a lock.

12. An electric shock cover, comprising:

a cover body formed with a protective space that matches a shape of a penis, the protective space being formed with an inlet;

a control board;

a battery assembly for powering the control board;

an electrically conductive silicone ring disposed at the inlet, wherein the electrically conductive silicone ring is in electrical contact with the control board; and a first electrically conductive silicone block is removably disposed in the first ventilation channel on the cover body at a tail which is opposite the inlet and with which the penis comes into contact when the penis erects upward, and surrounds the protective space together with the cover body, and in electrical contact with the control board such that the erected penis comes into contact with the first electrically conductive silicone block to effect an electric shock to the penis, wherein the first electrically conductive silicone block has at least one hollowed-out portion, and the protective space communicates with the outside air through the hollowed-out portion.

13. The electric shock cover according to claim 12, wherein the cover body is further provided with a control switch electrically connected to the control board.

* * * * *